(12) United States Patent
Goldmann et al.

(10) Patent No.: US 7,351,196 B2
(45) Date of Patent: Apr. 1, 2008

(54) INCONTINENCE STRIP FOR TREATING URINARY INCONTINENCE

(75) Inventors: Helmut Goldmann, Tuttlingen (DE); Erich K. Odermatt, Schaffhausen (CH); Christine Weis, Tuttlingen (DE); Werner Woelfle, Bad Duerrheim (DE); Hansjoerg Melchior, Kassel (DE); Wolfgang Abele, Tuttlingen (DE)

(73) Assignee: Aesculap AG & Co. KG, Tutlingen (DE)

(*) Notice: Subject to any disclaimer, the term of this patent is extended or adjusted under 35 U.S.C. 154(b) by 213 days.

(21) Appl. No.: 10/485,567

(22) PCT Filed: Aug. 1, 2002

(86) PCT No.: PCT/EP02/08570

§ 371 (c)(1),
(2), (4) Date: Jun. 22, 2004

(87) PCT Pub. No.: WO03/013392

PCT Pub. Date: Feb. 20, 2003

(65) Prior Publication Data

US 2004/0249240 A1   Dec. 9, 2004

(30) Foreign Application Priority Data

Aug. 3, 2001   (DE) ............................... 101 38 950
Mar. 23, 2002   (DE) ........................... 202 04 669 U (51) Int. Cl.
*A61F 2/02* (2006.01)

(52) U.S. Cl. ...................................................... 600/30

(58) Field of Classification Search ............ 600/29–31, 600/37; 128/885, 897; 606/119
See application file for complete search history.

(56) References Cited

U.S. PATENT DOCUMENTS

| | | | |
|---|---|---|---|
| 4,587,954 A | 5/1986 | Haber | |
| 4,709,690 A | 12/1987 | Haber | |
| 5,112,344 A | 5/1992 | Petros | |
| 5,899,909 A | 5/1999 | Claren et al. | |
| 6,030,393 A | 2/2000 | Corlew | |
| 6,042,534 A | 3/2000 | Gellman et al. | |
| 6,110,101 A | 8/2000 | Tihon et al. | |
| 6,432,040 B1* | 8/2002 | Meah ........................ | 600/37 |
| 6,475,139 B1 | 11/2002 | Miller | |
| 6,491,703 B1 | 12/2002 | Ulmsten | |
| 6,494,887 B1 | 12/2002 | Kaladelfos | |
| 6,652,450 B2* | 11/2003 | Neisz et al. ................. | 600/30 |
| 6,786,861 B1 | 9/2004 | Pretorius | |
| 2002/0099258 A1* | 7/2002 | Staskin et al. ............... | 600/29 |
| 2002/0165566 A1 | 11/2002 | Ulmsten | |
| 2002/0193517 A1* | 12/2002 | Wang et al. ................. | 525/63 |
| 2003/0004391 A1 | 1/2003 | Anazawa et al. | |

(Continued)

FOREIGN PATENT DOCUMENTS

DE           42 20 283 C2      12/1993

(Continued)

*Primary Examiner*—Charles A. Marmor, II
*Assistant Examiner*—Christine D. Hopkins
(74) *Attorney, Agent, or Firm*—Gary M. Nath; Tanya E. Harkins (57) ABSTRACT

The invention relates to a an incontinence strap (66) for treating urinary incontinence, in particular, urinary incontinence in females, that is configured such that it is flexible.

42 Claims, 8 Drawing Sheets

U.S. PATENT DOCUMENTS

2003/0004395 A1    1/2003    Therin

FOREIGN PATENT DOCUMENTS

| | | |
|---|---|---|
| DE | 101 03 179 A1 | 7/2001 |
| DE | 199 64 081 A1 | 7/2001 |
| DE | 201 09 379 U1 | 10/2001 |
| EP | 0 437 481 B1 | 7/1991 |
| EP | 0 639 355 A1 | 2/1995 |
| EP | 0639355 A1 | 2/1995 |
| EP | 1093758 A1 | 4/2001 |
| EP | 1108393 A2 | 6/2001 |
| FR | 2 802 798 | 6/2001 |
| FR | 2 814 939 | 4/2002 |
| GB | 2359256 A | 8/2001 |
| WO | 90/01016 | 2/1990 |
| WO | 91/00069 | 1/1991 |
| WO | 98/35632 | 8/1998 |
| WO | WO 98/35632 | 8/1998 |
| WO | WO 00/09039 | 2/2000 |
| WO | 00/18319 | 4/2000 |
| WO | WO 00/27304 | 5/2000 |
| WO | 00/74633 A2 | 12/2000 |
| WO | WO 00/74613 A1 | 12/2000 |
| WO | WO 01/45589 A1 | 6/2001 |
| WO | 02/065921 A1 | 8/2002 |

\* cited by examiner

INCONTINENCE STRIP FOR TREATING URINARY INCONTINENCE

BACKGROUND OF THE INVENTION

1. Field of the Invention

The invention relates to an incontinence strap for treating urinary incontinence, in particular, urinary incontinence in females.

2. Description of Related Art

Various operative methods and specially designed operating utensils and implants have been developed for remedying urinary incontinence. Several operative methods require opening the abdominal cavity in order to introduce items, similar to prostheses, that either encircle the urethra in the vicinity of the neck of the bladder or press against it from above or below (cf. WO 00/18319, WO 90/01016, WO 91/00069, U.S. Pat. No. 4,709,690, and WO 85/02993).

The so-called "plastic rein" was developed in the 1960's. In the case of this particular device, a strap that is wrapped around the underside of the urethra in order to raise the bladder, along with the neck of the bladder, which will be particularly helpful if the bladder has sagged, is attached within the abdominal cavity. The minimally invasive introduction of an incontinence strap in the form of a U-shaped noose that reaches around the underside of the urethra and, for example, in the case of female patients, is emplaced in the abdominal cavity by inserting it through the wall of the vagina, where the free ends of the noose terminate on the peritoneum, but, for the time being, are not attached thereto, has proven particularly beneficial. The strap is anchored by the ingrowth of connective tissue. Such straps and the associated instruments for inserting them into the lower abdomen are described in WO 90/03766, WO 96/06567, WO 97/13465, and WO 2001/030246.

SUMMARY OF THE INVENTION

The subject matter of the invention is an incontinence strap for treating urinary incontinence, in particular, urinary continence in females, whose properties yield further opportunities for its application and supplementary benefits.

The incontinence strap is designed to be flexible and consists of biocompatible material. It may be a textile strap, in particular, such that is coated or impregnated. The coating or impregnation may serve to ease introduction of the, inherently, open-pored strap, in particular, due to the presence of a smooth surface. The coating or impregnation may consist of biodegradable and/or resorbable material. The incontinence strap may also be in the form of a strip of foil that has a smooth, closed surface over at least part, or portions, of its length. Its surface may be textured in order to anchor it. In the case of a preferred embodiment, the materials employed and/or its construction may vary over its length. It may also have a shape that varies over its length and/or longitudinal sections having varying properties. A matter that is of particular importance to its longitudinal midsection, which is intended to be arranged in the vicinity of the urethra. The strap is usually wrapped around the underside of the urethra. However, embodiments that may be arranged above the urethra are also feasible, particularly if their thickness is variable, a matter that shall be taken up below.

Since the urethra is highly sensitive to irritations and such irritations may cause undesirable proliferation of tissue, the midsection of the strap preferably has a smooth surface. Part(s) of the strap, in particular, its midsection, which is intended to be arranged in the vicinity of the urethra, may consist of resorbable material, in particular, resorbable plastic. Mechanical irritations caused by the incontinence strap due to, for example, its surface texturing and/or pores, and/or irritations of biological origin occurring during resorption as a result of accelerated metabolic processes, may cause growth of new connective tissue that will yield a desired lifting, or supporting, of the urethra. This supporting connective tissue may take over the task of an incontinence strap, in which case, the latter will no longer be needed. At least part of the strap will disappear due to resorption. If it consists entirely of biodegradable or resorbable material, then all of it will disappear in the course of time. If just its midsection consists of resorbable material and its other sections at least partially consist of non resorbable material, then those other sections may remain in the body indefinitely.

The resorbable materials employed are preferably of non biological origin, in particular, resorbable plastics, in order to prevent infections and defensive immuno-reactions. Known polymers and copolymers of lactide, glycolide, trimethylene carbonate, dioxanone, and $\epsilon$-caprolactone represent suitable plastics. Also particularly suitable is polyvinyl alcohol, whose solubility and resorption rate may be influenced by suitably choosing its molecular weight, chemical modification, and/or physical treatment (formation of crystallites by cyclic freezing and thawing).

The strap may also be configured from several, longitudinal, essentially parallel strips having differing resorbabilities in order to, in particular, eliminate foreign matter as soon as it is no longer needed. Variations occurring along the length of the incontinence strap, in particular, variations affecting its longitudinal midsection, may also be related to the mechanical properties of the strap. For example, the lateral edges of the strap may beneficially be smooth, at least along its longitudinal midsection. The other longitudinal sections of the strap may have textured edges and/or surfaces in order to provide better anchoring. For example, its longitudinal midsection preferably has a closed, in particular, smooth, surface. Its longitudinal midsection of the strap may also have a width and/or thickness exceeding those of its other sections.

In the case of a special embodiment of the invention, the strap is configured such that its thickness may be varied, in particular, may be varied at least over, and particularly over its midsection. The longitudinal midsection of the strap may be double-walled, preferably tubular. This double-walled, and, in particular, tubular, construction may be provided over the entire length of the strap. In the case of a preferred embodiment, the strap has a chamber that may be filled with fluid located on its longitudinal midsection. The chamber may expand and contract when the volume of fluid contained therein is varied, due to its flexible walls. The tubing, or the chamber's walls, may also be at least partially formed from elastic, stretchable, material. The walls of the chamber that may be filled with fluid may also at least partially consist of a material, in particular, silicone rubber, that is pierceable by a cannula and self-sealing, which will allow subsequently, i.e., subsequent to emplacement of the strap in the body, altering the chamber's size and shape by adding, or drawing off, fluid. The embodiment having a variable thickness is also suitable for emplacement above the urethra, and may be used for exerting pressure on the urethra, without encircling it.

The chamber that may be filled with fluid may also be provided with a fluid line, through which its fill level may be altered, extending to at least one end of the strap. Such a chamber and a fluid line connected thereto may, in the case of a strap fabricated from thermoplastic foil, be formed by welding the walls of tubing having the desired contouring, which will also be possible in the case of straps fabricated from thermoplastic elastomers. In the case of pure elastomeric materials, the chamber, and the fluid line, if any, may be formed either when the strap, in particular, tubing, is fabricated, or by subsequent vulcanization thereof.

The ends of the incontinence strap may be sutured to the abdominal wall in the traditional manner. However, it will be preferable if they will self-anchor to the abdominal wall. Those sections of the incontinence strap that are intended to be arranged in the abdominal wall, i.e., sections thereof in the vicinities of its ends, may have a crinkled surface and/or porous structure that will promote self-anchoring in the abdominal wall. Such crinkled surfaces promote both mechanical retention by connective tissue and additional anchoring by ingrowth, or penetrative growth, of new tissue.

The strap is preferably configured such that it may be drawn through the abdominal cavity, in particular, the vicinity of the urethra, employing minimally invasive operating techniques, i.e., without opening the abdominal cavity. It will be beneficial if both ends of the strap are configured for attachment to a shaft, in particular, a curved shaft, to be used for emplacing the strap within the abdominal cavity. The ends of the strap may be reinforced for that purpose. The ends of the strap may also be narrower than the remainder of the strap. The ends of the strap may be provided with a hole, a matter that shall also be taken up in greater detail later in conjunction with the descriptions of other embodiments. The ends of the strip may also be attached to couplers that may be attached to the shaft.

In the case of a preferred embodiment of the invention, the strap is attached to the shaft such that it cannot twist, which will allow predetermining an orientation of the strap during its insertion into the lower abdomen.

The strap may preferably be attached to the shaft such that the plane of the strap lies in the plane of flexure of the shaft. The strap may be such that it may be attached to the shaft over its full width, particularly if the shaft is also configured such that it has a flat shape. In the case of shafts having an essentially circular cross-section, the orientation of the strap may also be predetermined by folding its ends such that they will have U-shaped, V-shaped, or Z-folded cross-sections, which will provide that the orientation of the contours of the strap will be predetermined over the remainder of its length. For example, the strap may be attached, in a predetermined form, to couplers that may be attached to the shaft such that they cannot twist. The ends of the strap may be narrower than the remainder of the strap in order to ease insertion. The ends of the strap may be stiffer than the remainder of its flexible section.

In the case of a preferred embodiment of the invention, the strap and, in particular, the coupler(s), is/are permanently attachable, or attached, to the shaft. This will provide that a shaft may be used only once during an operation, which is preferable on hygienic grounds.

In the case of another embodiment, the strap is arranged in a sheath that is configured such that it may be withdrawn from the strap. The sheath both protects the strap and eases insertion of the strap into the lower abdomen, particularly if the strap has a textured outer surface or has any rough spots on its outer surface. The sheath is preferably transversely split at its midsection, or may be transversely split there, in order that a segment of the sheath on either end of the strap may be withdrawn from the strap following implantation of the strap. The ends of the sheath may be permanently attached to the strap in order that segments of the sheath will remain accessible after the ends of the strap have been cut off the shaft. The ends of the strap may also be allocated to devices for securing the strap outside the abdominal wall. Such securing aids may serve to secure the ends of the strap outside the abdominal wall while the sheath is being pulled over its ends. They may be, for example, strap extensions, temporary thickenings, or mechanical braking mechanisms, such as slit rubber buttons.

A grip, to which the shaft may be attached, in particular, attached such that it will be secured against both axial and rotational displacements, and subsequently detached, may be associated with the shaft. The shaft may have insertion tips for penetrating the lower abdomen on both ends, or be configured to allow attaching such thereto. The shaft may also be configured such that either end thereof may be attached to the grip and subsequently detached therefrom. The shaft may additionally configured such that a strap may be attached to either end thereof, which will allow using either end of the shaft for penetrating the lower abdomen, attaching the grip, or attaching the strap. In the case of a detachable union of shaft and grip, it will be preferable if the strap may be attached to an end of the shaft only while the grip is removed from that end of the shaft.

As mentioned above, it may be provided that the shaft may be used once only, at least during a single surgical session. Each end of the strap is thus preferably allocated to its own shaft. A safety device that will preclude reuse of the shaft during an operation may be provided. The end of the strap, in particular, the coupler thereon, may be configured such that it may be attached to the shaft such that it cannot be subsequently detached therefrom for that purpose. If the strap becomes detached from the shaft, the end of the strap, or coupler, will remain on the shaft when the strap becomes detached from the shaft and preclude the latter's reuse, since attaching another strap thereto will be precluded. The end of the strap and the coupler are preferably configured in the form of mating, plug-and-socket connectors. The union between shaft and strap may be self-locking in order that it cannot be separated without use of special tools.

The shaft normally has a circular cross-section. However, as mentioned above, the shaft may have a noncircular cross-section within a section thereof that is intended for insertion into the body. In particular, the shaft's cross-section may have an extension in one direction that is much greater than that in the orthogonal direction. This broadening may be orthogonal to the plane of curvature of the shaft, but preferably lies in the plane of curvature of the shaft, which will favor oriented insertion of the strap into the lower abdomen, in particular, oriented penetration of strap through the abdominal wall. For example, a longitudinal section of the shaft may have a width that approximately equals the width of the strap to be attached thereto. The shaft may also be broadened over its entire length. The shaft may also be broader than the strap over at least certain sections thereof, which is preferred in the case of adipose patients. Any changes in the width of the strap should preferably be gradual.

The shaft and grip may also be permanently joined to one another, in particular, may be configured in the form of a single, monolithic unit. A device for attaching the strap may then be provided on the free end of the shaft. That device preferably has a securing mechanism that will prevent unintentional detachment of the strap.

In the case of another embodiment, the shaft may be enclosed in a flexible sheath, from which the shaft may be withdrawn, in particular, may be withdrawn when the strap is pulled through the sheath. The shaft's flexible sheath may consist of resorbable material and be designed to temporarily remain in the body. The flexible sheath may also be designed to be itself an incontinence strap, in which case, at least part of the strap, along with the shaft, may be inserted into the lower abdomen.

In the case of another preferred embodiment of a strap having a sheath, at least one end of the strap has an attachment device for attaching the strap to application aids provided for the purpose of assisting its emplacement in the abdominal cavity. The strap is beneficially reinforced in the vicinity of that device. The reinforced attachment device preferably has a low profile and is situated in the plane of the strap.

As stated above, the strap is preferably configured such that it may be drawn into the abdominal cavity, in particular, into the vicinity of the urethra, through the vaginal wall or abdominal wall, employing minimally invasive surgical techniques, i.e., without opening the abdominal cavity. In order to allow emplacing the strap at the right location in the body as simply as possible and in a manner that will be gentle to the patient, the strap is usually implanted using application aids. These application aids are usually attached to the ends of the strap and, in addition to the aforementioned shafts, may also consist of, for example, implantation needles or cords. The reinforcements in the vicinity of the attachment device on the incontinence strap according to the invention prevent tearing of the strap in the vicinities of the attachment devices due to the effects of tensioning by the application aids.

The incontinence strap is preferably reinforced in the vicinity of the attachment device by thermally bonding it to another material (In this conjunction, "thermally bonding" one or more materials to the strap means that one or more materials are thermally softened, or melted, and flow into the pores of the unmelted strap and harden there). The strap is thermally bonded to the sheath of the incontinence strap, in particular, thermally bonded thereto in that vicinity. Such thermal bonding of the strap to the sheath in the vicinity of the attachment device allows reinforcing the strap in that vicinity in a simple manner. Employing other weldable material in the process may also modify its flexibility.

In order to further reinforce the strap in the vicinity of the attachment device, additional, thermally bondable material, in particular, thermoplastic material, may be employed in the process. In the case of a preferred embodiment of an incontinence strap according to the invention, at least the sheath may be folded over in the vicinity of the attachment device and thermally bonded to the strap. This folding over may be accomplished in various manners. For example, the corners of the sheath may be folded over in order to configure the reinforcement in the form of an equilateral triangle, which has the benefit that the incontinence strap will then have tapered ends, and thus may be more easily drawn through tissue, while maintaining its orientation. In the case of another embodiment, the edges of the ends of the sheath may be folded over in order that the reinforcement will have a rectangular, or square, shape. In the case of yet another embodiment, both the corners and edges on the ends of the sheath may be folded over, which will yield particularly strong reinforcements in the vicinities of the attachment devices.

An embodiment where both the sheath and the ends of the strap are folded over, which will yield even greater strengthenings in those vicinities, will also be feasible.

In the case of yet another preferred embodiment, the ends of the strap are rounded. The end, or ends, of the strap may be shaped by thermal cutting.

It will be beneficial if the strap, in particular, the sheath, is encased in at least one other ply, preferably several plies, of thermally bondable material(s), in particular, in at least one other sheath, in the vicinities of the attachment devices and at least partially thermally bonded thereto. This will contribute to further reinforcing it in the vicinities of the strap's attachments devices. It will be beneficial if at least one of the plies has a film thickness exceeding that of the sheath. These plies also preferably consist thermally bondable, thermoplastic material.

The types of bonds, with which the reinforcements in the vicinities of the attachment devices may be accomplished, may differ. As a rule, they will be bonds that cover extended areas, and will preferably be flexible. Bonds that cover extended areas should preferably allow bending them through 180° without fracturing occurring. If required, the bonds may also be a set, or sets, of partial bonds, each of which covers an extended area, or point bonds in order to allow configuring them such that certain portions thereof will be more flexible and softer. Combinations of the various types of bonds will also be feasible. It will be beneficial if the plies to be bonded may consist of materials having differing softening ranges or melting ranges in order that, in the case of certain bonds, certain plies will preferentially soften or melt. For example, in the case of a preferred embodiment, initially, a basic bond in the vicinities of the attachment devices may be formed at a low temperature, at which, initially, only the low-melting-range plies, e.g., the sheath, which may consist of polyethylene, will soften. Following completion of this basic bond, a set, or sets, of partial bonds, each of which covers an extended area, in the vicinity thereof may be formed at a higher temperature. Point bonding at an even higher temperature, e.g., at a temperature at which the material of the strap, which may consist of polypropylene, polyethylene terephthalate, PVA, or other non absorbable, or absorbable, polymers, such as polylactides, polydioxanones, or mixtures of glycolides, lactides, caprolactones, or similar, will soften, may then be formed over certain sections in the vicinity/vicinities of the set(s) of partial bonds. Such combinations of bonds covering extended areas, set(s) of partial bonds, each of which covers an extended area, and point bonds will allow forming reinforcements that are stiffer at their centers than at their edges, which will allow achieving spatially varying flexibilities. The strap may be in the form of a textured foil or a fabric, and preferably has a softening range that lies at higher temperatures than both that of the sheath and that/those of the reinforcing material(s), if any.

In the case of a particularly preferred embodiment of the incontinence strap according to the invention, the attachment device has at least one through hole in the vicinity of the reinforcement. An application aid, for example, a cord, may be attached to this hole, or a surgical instrument may enter through it. The through hole may be punched, but is preferably formed by thermal cutting, and beneficially has an edge zone where all plies are permanently bonded to one another. Unlike the known straps, which have permanently attached application aids, the strap according to the invention provides the benefit that the application aid may be attached to it in a simple manner, subsequently detached therefrom, and reused. In the case of the aforementioned combination of bonds covering extended areas, set, or sets, of partial bonds, each of which covers an extended area, and point bonds, a through hole is punched in the vicinity of the bonds, in particular, in the vicinity of the point bonds. The through hole may have various shapes, in particular, may have an angular shape, but is preferably circular or oval.

The dimensions of the ends of the incontinence strap are preferably less than those of the sheath enclosing the incontinence strap.

In the case of a particularly preferred embodiment of the incontinence strap according to the invention, at least the sheath, and other material or other plies employed, if any, consist of thermoplastic material. It will be beneficial if the strap consists of thermoplastic material whose melting range lies at temperatures exceeding those of the melting range of the plies lying on the strap. The material involved may be either a material that is totally resorbable by the body, a material that is partially resorbable by the body, or a material that is non resorbable by the body.

Other features of the invention will be evident from the following descriptions of embodiments of the invention, together with the figures and subordinate Claims, where the individual features involved may, in the case of an embodiment of the invention, be implemented either alone, or in the form of combinations of several such.

BRIEF DESCRIPTION OF THE DRAWINGS

The figures depict.

DETAILED DESCRIPTION OF PREFERRED EMBODIMENTS

In the case of the embodiment of an instrument 1 for emplacing an incontinence strap 2 shown in FIGS. 1-9, a shaft for inserting the incontinence strap is provided in the form of a curved, solid, stainless-steel needle 3 in the form a curved, circular rod 4. The needle has a conical tip 6 on an insertion end 5. That may also be ground off at an angle such that the edge of the ground-off section lies on the inner side of the curvature. The tip of the needle is not sharp in order to prevent injuries to the abdominal organs when the incontinence strap is inserted. Since incisions in the abdominal wall and vaginal wall will, in any case, be made using other instruments, such as scalpels, the needle essentially acts as a guiding appendage only. The end of the needle opposite that bearing the tip 6 is configured in the form of an attachment end 7 and has devices for attaching it either to a grip 8, or to the incontinence strap 2.

The grip 8 consists of plastic or steel. It has a longitudinal section 9 that is essentially configured in the form of a hollow cylinder that is used both for accommodating and attaching the end 7 of the needle, and for gripping with the hand. The butt of the grip has a laterally broadened section 10 that essentially gives the grip a T-shape, is also used for gripping, and allows precisely controlled, lateral excursions of the needle.

Figure 7:
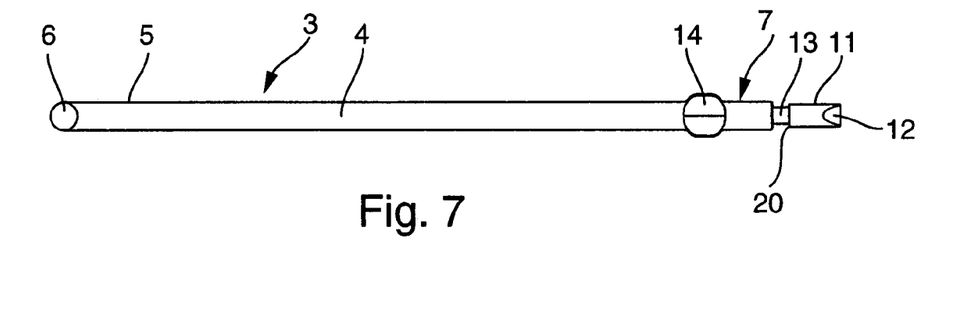
FIG. 7: the shaft, viewed normal to its plane of curvature.

As may be seen from FIG. 7, the attachment end 7 of the needle 3 has a cylindrical section 11 having a diameter that is less than the normal diameter of the needle, has a beveled surface 12 on one side, or either side, and is separated from the circular rod 4 of the needle 3 by a circumferential groove 13 that forms an intervening cylindrical section having an even smaller diameter. This end of the needle is also is provided with an anti rotation lug that has a cross-section differing from the circular cross-section of the needle, in particular, an anti rotation lug in the form of a stamped flat 14, in the vicinity of that section of the needle where the needle has its full diameter.

Figures 1, 2:
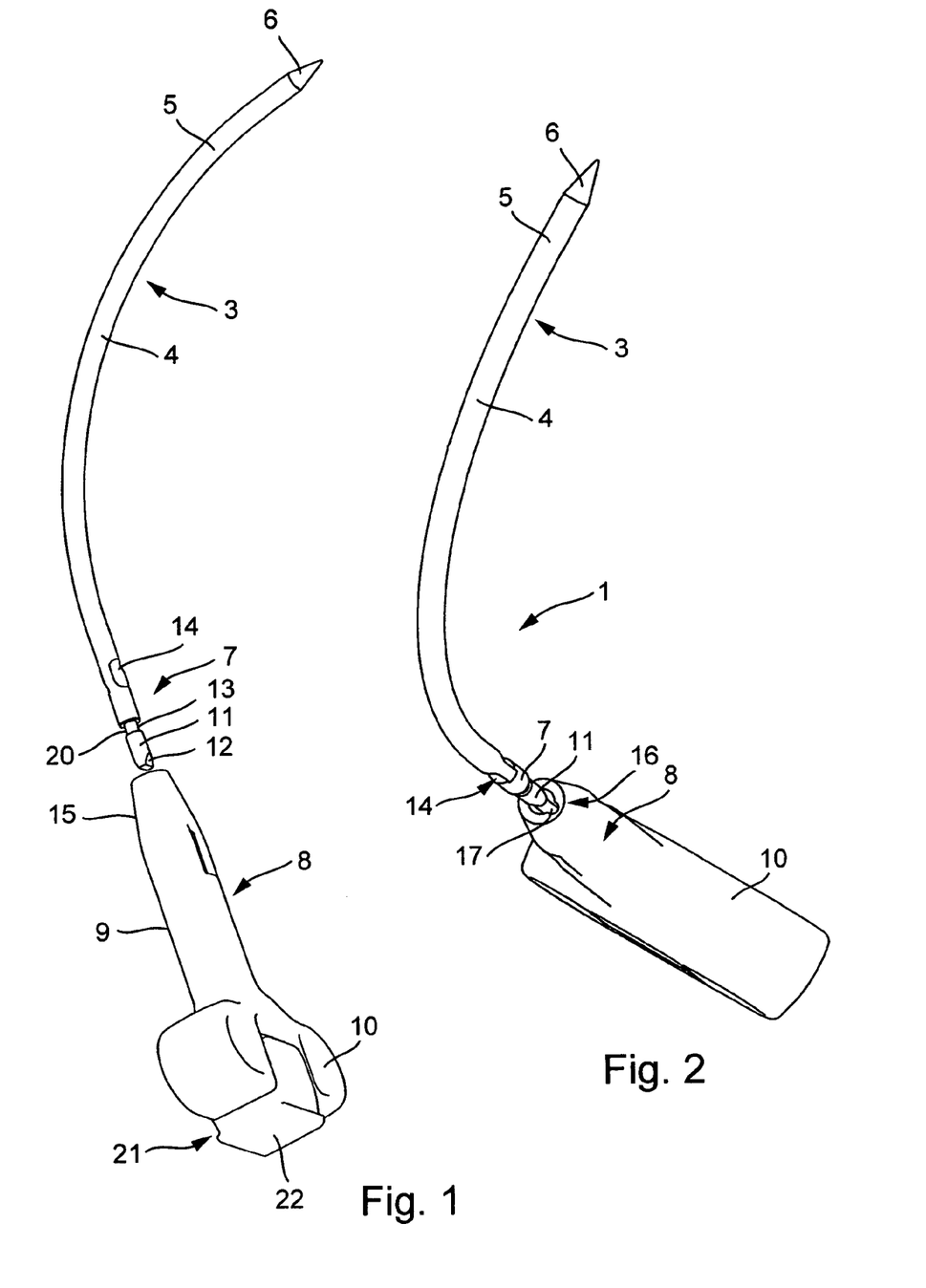
FIG. 1: a perspective view of an embodiment of an instrument for inserting an incontinence strap that has a curved shaft and a handling grip for the shaft, which is shown here with the shaft and grip separated.
FIG. 2: another perspective view of the embodiment shown in FIG. 1.
Figure 3:
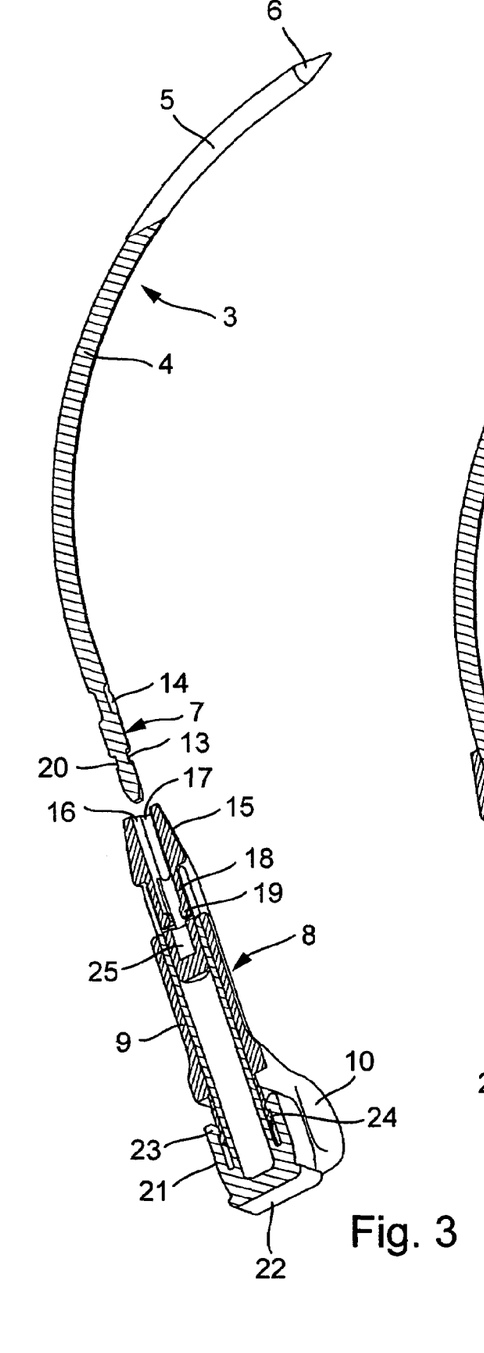
FIG. 3: a sectioned view of the same arrangement of shaft and handling grip shown in FIG. 1.

The grip 8 is symmetric with respect to the central plane of intersection orthogonal to the plane of the "T" and has in its interior a receptacle for holding the needle. For that purpose, on its conically tapered attachment end 15 the grip has an insertion bore 16 whose inner diameter equals the normal diameter of the needle and also has a pair of lateral, flat-bottomed, longitudinal grooves 17 whose dimensions equal those of the stamped flat 14 on the needle and guarantee seating of the needle such that it will be constrained from rotating and be in the correct orientation with respect to the grip. When in that orientation, the plane of curvature of the needle is orthogonal to the plane of the T-shaped grip.

Figure 4:
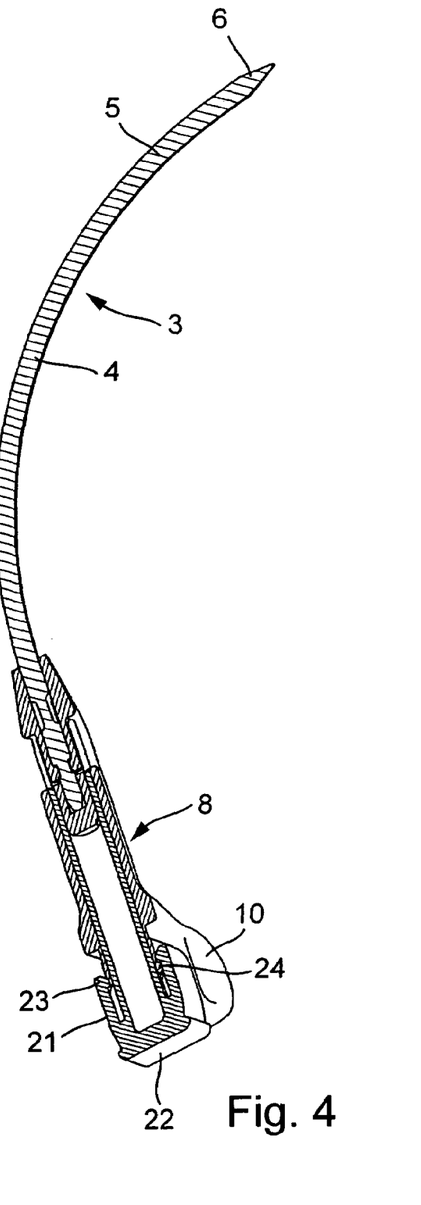
FIG. 4: a longitudinal section through the shaft and grip, where the shaft has been inserted into the grip, but has not yet been locked therein.
Figure 5:
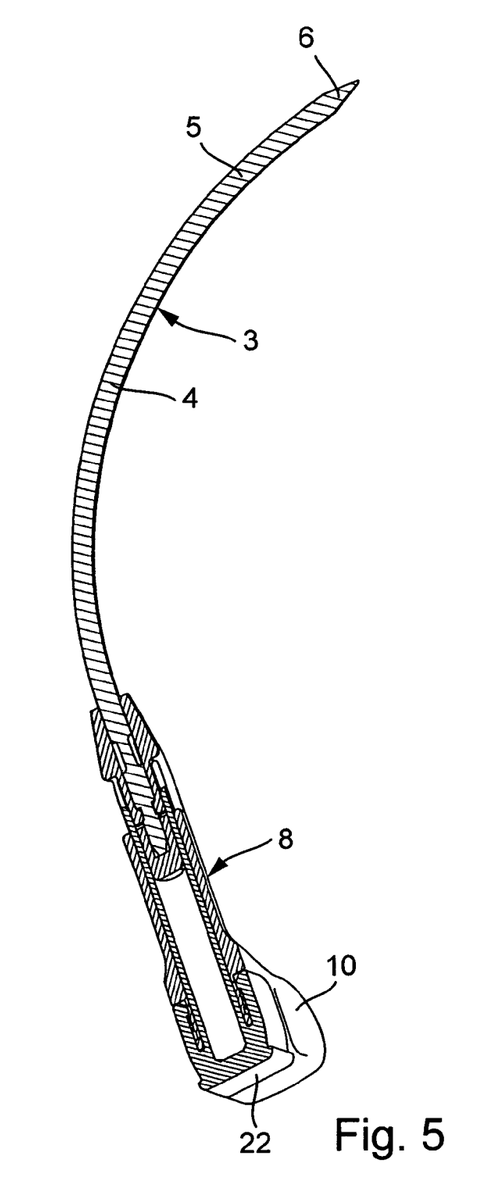
FIG. 5: a longitudinal section through the shaft and grip, where the shaft and grip are in the locked state.
Figure 6:
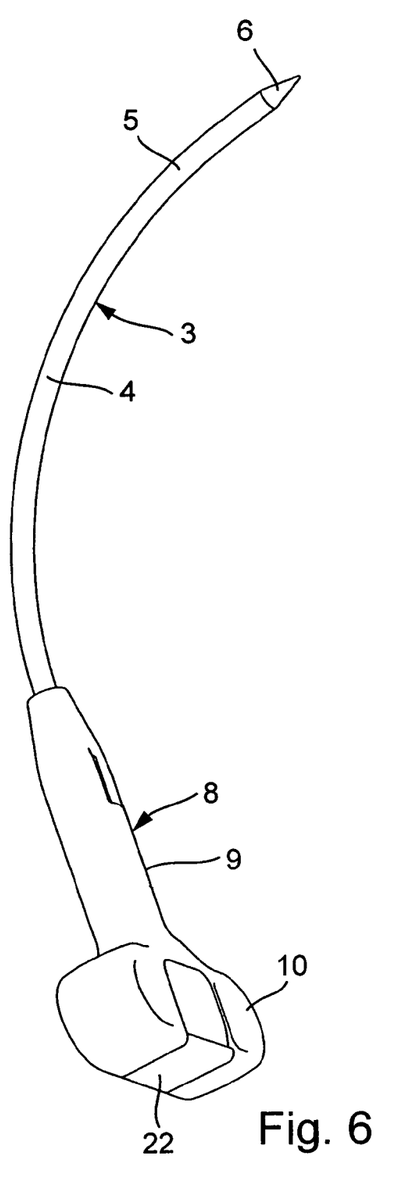
FIG. 6: a perspective view of the shaft and grip, where the shaft and grip are in the locked state.

The walls of the hollow, cylindrical, longitudinal section 9 of the grip have a pair of thinner sections formed by mirror-image, with respect to the plane of the "T," window-like recesses on diametrically opposite sides that are configured in the form of detenting prongs 18. These detenting prongs 18 are longitudinal leaf springs whose end facing the insertion aperture of the grip forms a unit with the material of the longitudinal section 9 and whose free end has a detenting protuberance 19 that faces inward. As shown in FIG. 4, the detenting prongs 18 latch into position with their detenting protuberance 19 situated in the circumferential groove 13 on the end 7 of the needle, but are not self-locking. On the contrary, their detenting protuberances 19 have flats on their sides facing toward, and away from, the direction of insertion, and may be flexed and spread apart both by the beveled surfaces 12 on the end of the needle aligned on them when the end 7 of the needle is inserted and by the shoulder 20 on the circumferential groove 13 when the end 7 of the needle is withdrawn. The detenting prongs are locked by a slide 21 in the form of a sleeve arranged within the grip that may be slid along the longitudinal axis of the grip that engages the outer surfaces of the detenting prongs 18 when in its locking position (cf. FIG. 5) and rests with its engaging, free end 22 abutting against the broadened section 10 on the end of the grip, where it self-locks onto the housing of the grip by flexing. In the disengaged position (cf. FIGS. 3 and 4), the slide 21 releases the detenting prongs 18 and overlaps the end of the grip. Detenting elements 23 on the slide, together with associated active elements 24 on the grip, prevent the slide 21 from falling off the grip when in its disengaged position. The grip may be disassembled for cleaning, i.e., the slide 21 may be slid over the active elements 24 on the grip 8 and off the grip in order to remove it. The interior of the grip also has a hollow section 25 that has an inner diameter that is less than that of the grip and equals the outer diameter of the cylindrical section 11 on the end 7 of the needle, and serves as a receptacle for that cylindrical section, which guarantees wobble-free seating of the needle in the grip.

Figure 8:
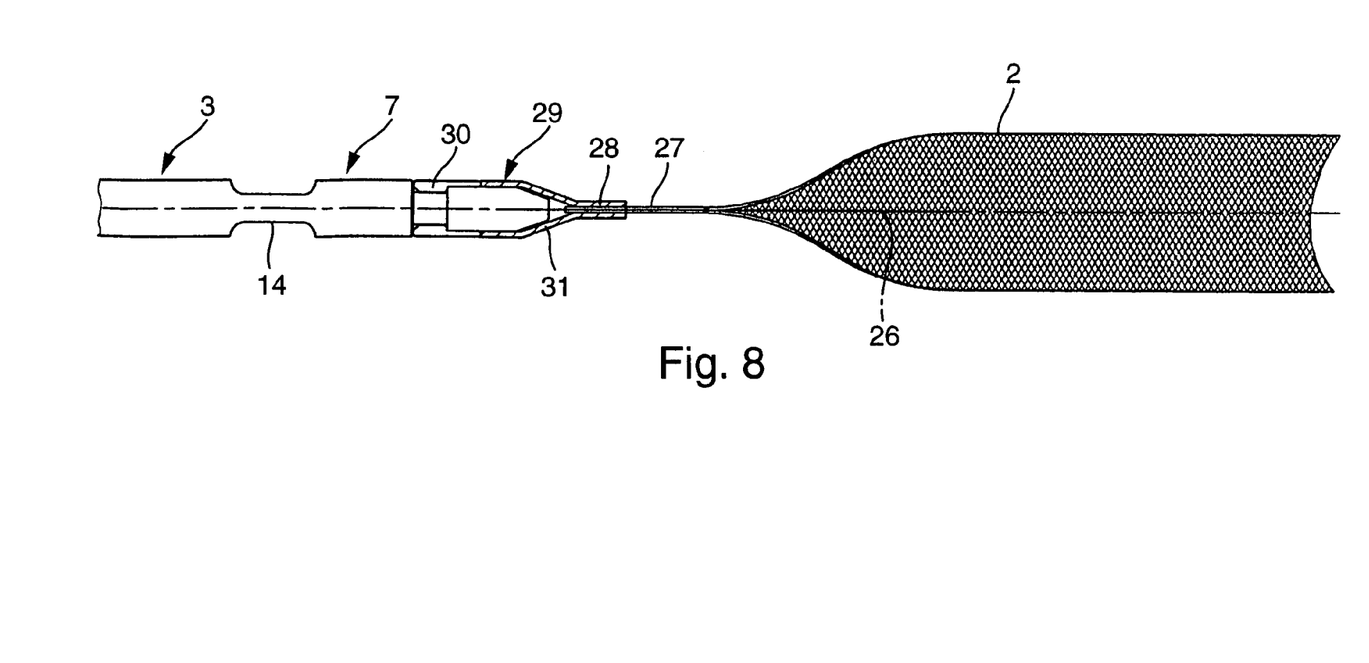
FIG. 8: a view of part of the shaft, where an incontinence strap has been attached thereto.

The strap 2 is formed from a flat strip of cloth netting. Both ends of the strap are folded along the centerline 26 of the strap in order that its end sections 27 will be half as wide as the remainder of the strap and their planes will be orthogonal to the plane of the strap. These end sections 27 are firmly clamped in the flattened ends 28 of a retaining sleeve 29 on the end 7 of the needle that fits on the cylindrical section 11 thereof having a smaller diameter, and latches into position thereon. The retaining sleeve has the same outer diameter as the circular rod 4 of the needle. The free end 30 of the retaining sleeve 29 is longitudinally slit, where the tips of the prongs formed thereby are either bent inward or configured such that they are thicker, snap into place in the circumferential groove 13 on the end of the needle, and reach around, and abut against, the circumferential shoulder 20, in order that it may be attached to the end 7 of the needle. The strap 2 may be attached to the needle 3 such that it cannot twist, in particular, is attached thereto oriented such that the plane of the strap lies in the plane of curvature of the needle. The single flat 12 (cf. FIG. 7) or pair of flats on the cylindrical section 11 of the needle interact with the sloping surfaces 31 formed by the stamped flats on the retaining sleeve 29 for that purpose. However, other configurations of the anti twisting mechanism are feasible.

In the case of the embodiment of the invention shown, the means for attaching the strap may be such that they prevent successively attaching opposing ends of the strap to the same needle, i.e., prevent the same needle from being used twice during an operation. The retaining sleeve 29 on the end 7 of the needle is thus either permanently attached thereto, or may only be removed therefrom using a tool that has been specially designed for that purpose. This will preclude attachment of the other end of the strap to the end 7 of the needle and prevent reuse of the needle during the same operation. In the case of a permanent attachment of the strap to the needle, the needle 3, together with the retaining sleeve 29, are discarded after the strap 2 has been cut off. If the needle 3 is to be reused, the retaining sleeve 29 may be removed from the needle using the special tool before the needle is cleaned and sterilized.

Figure 9:
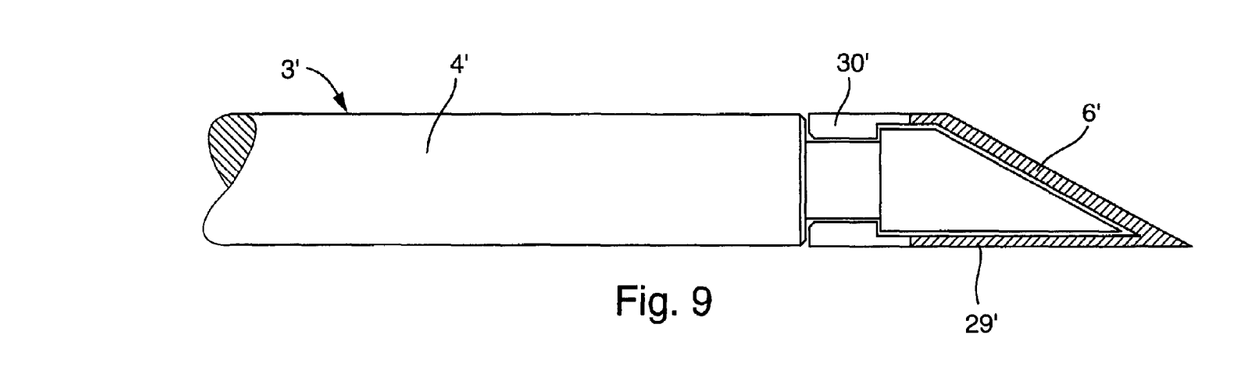
FIG. 9: a view of an end of a shaft of another embodiment that may either be attached to a grip, have an incontinence strap attached to it, or have a tip installed on it, drawn on a larger scale.

It may also be provided that the needle 3' has tips 6' on both ends by, for example, providing that its attachment end 7 is also pointed or has been ground off an angle. Alternatively, it may also be provided that tips for the needle are configured such that they may be attached to the needle 3', in particular, to the circular rod 4', as shown in FIG. 9. Both ends of the needle may be configured such that tips 6' may be attached thereto. For example, both ends of the needle may be configured similarly to its attachment end 7'. A sleeve 29' having a tip 6', instead of a retaining sleeve, may then be slipped onto the needle. It may also be provided that the tips are designed to be detachable and the retaining sleeve attached to the strap is slipped onto the needle once the tips have been detached.

The instruments shown in FIGS. 1-9 have a wide variety of applications due to the opportunities for varying their configurations that they provide, and may be used in surgery in which their shaft is inserted through the abdominal wall from above and guided downward, or, in the case of female patients, for example, inserted through the vaginal wall and guided upward to the abdominal wall from below. The strap may be pulled through by the needle, as in suturing, by guiding the needle through the lower abdomen and allowing the needle to transport the strap along with it. The strap may also be picked up by, for example, guiding the needle downward from the abdominal wall, attaching the strap to the accessible tip of the needle, and withdrawing the needle, along with the strap.

Figure 10:
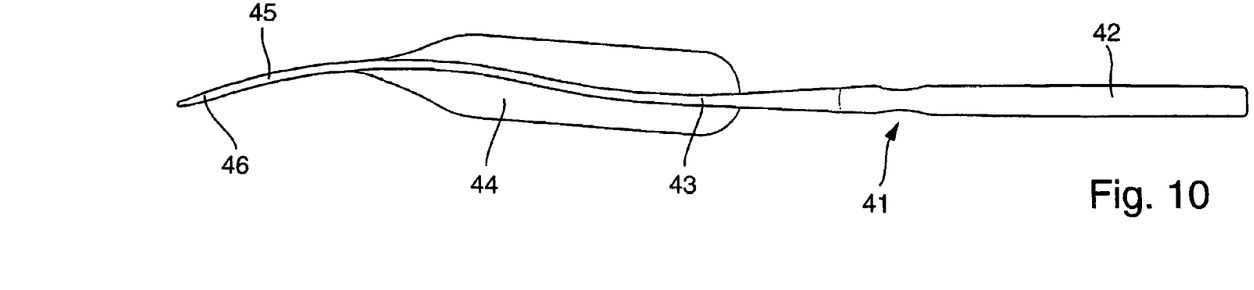
FIG. 10: a side view of another embodiment of an instrument for inserting an incontinence strap.
Figure 11:
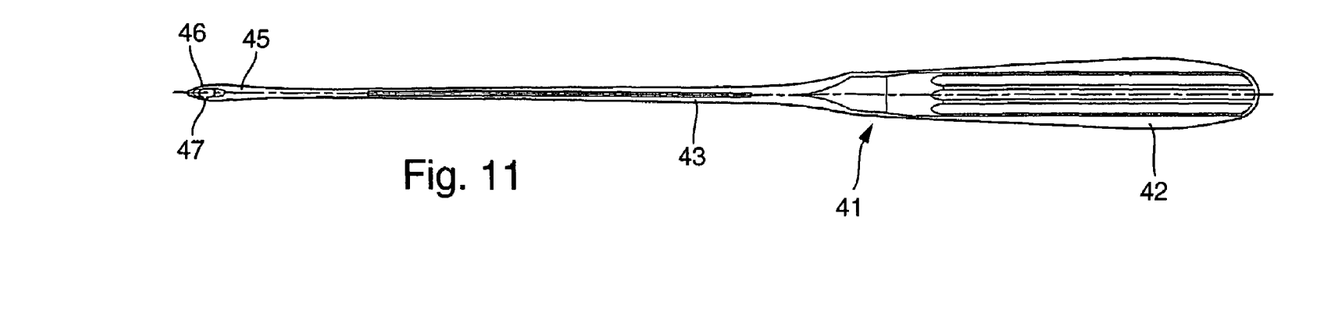
FIG. 11: a top view of the same embodiment shown in FIG. 10.

The embodiment of an instrument for emplacing an incontinence strap shown in FIGS. 10 and 11 has fewer prospective applications than the aforementioned instruments. However, the instrument 41 shown there is more simply constructed and has several special features. The surgical instrument 41 has a grip 42 and a shaft 43 that are configured in the form of a single, monolithic unit and beneficially consist of stainless steel. The grip 42 is long and flat, but may also have another shape suitable for use on surgical instruments. The shaft 43 follows a gentle S-curve. It has a broadened section 44 that is essential contiguous to the grip 42 in the form of a flat rod having blunt, parallel, lateral edges terminating in a curved section 45 having an essentially circular cross-section that has a hook 47 opening sideward for attaching an incontinence strap to its tip 46. The transition from the broadened section 44 to the narrow section 45 is gradual, and achieved by tapering the broadened section. The plane of the broadened section lies in the plane of curvature of the curved section 45. The lateral edges of the broadened section 44 curve slightly upward relative to those of the grip 42, and those of the curved section 45 on which it terminated curve slightly downward relative thereto. However, the shaft may also be configured in the form of a curved rod having an essentially circular cross-section.

The embodiment according to FIG. 10 is intended for use in cases where the shaft is guided through the abdominal wall and downward, into the abdominal cavity. The purpose of the broadened section 44 is giving the incision channel through the abdominal wall and the connective tissues and fatty tissues lying thereunder, and extending downward to the vaginal wall, a broadened shape that will roughly correspond to that of the incontinence strap. This broadening may essentially extend over the entire length of the shaft. Once the shaft has been inserted into the abdominal cavity, the strap may be attached to the tip 46 of the shaft 43, which has been guided through from below, for example, guided through the vaginal wall, and withdrawn along with the instrument when the instrument is withdrawn. In the case of two incisions in the abdominal wall, to the right and left of the center thereof, or, preferably, a central incision above the pubic bone, the ends of the strap on the right and left of the urethra, respectively, may be pulled upward, yielding a U-shaped noose reaching around the underside of the urethra.

The tip of the shaft may be configured such that it will allow attaching the strap such that the strap may be subsequently detached therefrom, in particular, may be configured such that it provides an attachment mechanism having a securing device that will prevent the strap from becoming unintentionally detached from the shaft. In the case of the embodiment shown, the tip 46 of the shaft is preferably configured in the form a so-called "Reverdin needle." The latter has an eye that may be opened and closed and has a hooked shape when in the opened state. However, the attachment mechanism on the tip 46 may also be configured differently, for example, by configuring the tip in the form of a simple eye, or by configuring the tip in the form of a detachable cap and providing that a coupling element, to which a mating coupling element on the strap may be attached, will be exposed when the tip is removed, as has been described in conjunction with FIG. 9. The eye may also be closed by means of a cap nut.

Figure 12:
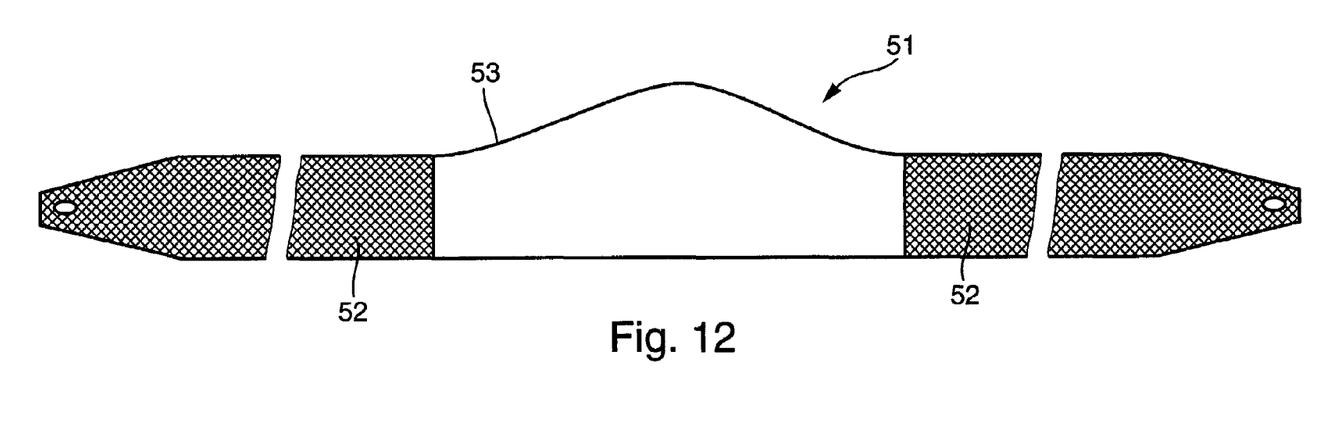
FIG. 12: an embodiment of an incontinence strap.

In the case of an embodiment of an incontinence strap according to FIG. 12, the incontinence strap 51 has longitudinal sections that differ from one another. Two end sections 52, each about 10 cm to 20 cm long and about 2 cm wide, are configured in the form of coarse-weave textile straps that have rounded or tapered, V-shaped ends and holes, or other facilities, for attaching them to an insertion instrument. A midsection 53 consists of resorbable plastic and is broadened, compared to its end sections 52, on one side by a sort of curved extension. This section consists of smooth foil material, has smooth edges. It is intended to reach around the underside of the urethra. Its smooth contours, and the fact that it has been designed to protect the urethra, will help prevent injuries to the urethra due to undesired, unrestrained proliferation of newly formed, connective tissue. Insertion of this section of the strap, which represents a foreign object, will provide that sufficient tissue for supporting the urethra from below will be formed. Since the implant will thus have served its purpose, this particular section of the strap may be configured from resorbable material.

The degradation period and resorption time of the material used for configuring the midsection may be predetermined in a known manner employing suitable copolymerization processes. The polymers that come into question are synthetic polymers, in particular, such that may be obtained by polymerizing lactide, glycolide, trimethylene carbonate, dioxanone, ε-caprolactone, or mixtures thereof.

Figure 13:
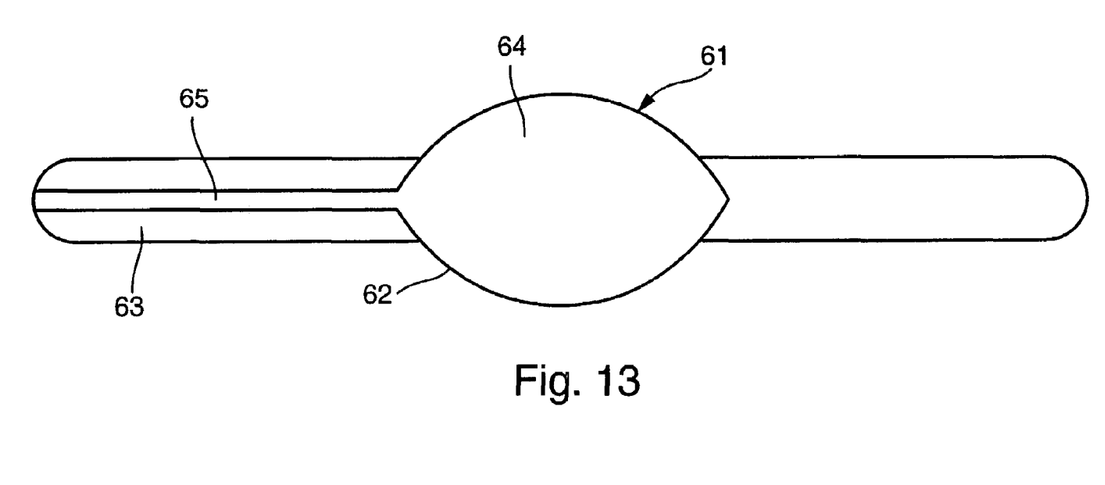
FIG. 13: another embodiment of an incontinence strap.

In the case of the embodiment shown in FIG. 13, an incontinence strap that is intended to remain in the body indefinitely is provided. Once again, the incontinence strap 61 is subdivided into various sections, where at least one midsection 62 is configured in the form of a chamber that may be filled with a fluid, for example, water or liquid contrast media. The midsection 62, or even the entire strap, may be configured in the form of a tube for that purpose. Various types of designs and materials are available for configuring the strap. In the case of the embodiment shown in FIG. 13, at least the strap's midsection and at least a channel section 63 bordering on its midsection consist of thermoplastic material. Seam-welding opposing walls of the tubing will allow configuring the chamber 64 and the communicating fluid channel 65 extending along the channel section 63, through which the chamber may be filled and the fill-volume of the chamber may be subsequently corrected whenever necessary. The fluid channel 65 may be closed, for example, welded closed, once the chamber has been filled. It may also be accessible beneath the abdominal skin via a valve, for example, a pierceable membrane, that is accessible from outside.

Alternatively, the chamber may also be formed from an elastomer, for example, silicone rubber, that is pierceable and self-sealing, in which case, no separate fluid channel will be required. It will also be feasible to configure the entire strap in the form of a tube and merely seal both ends. The only essential feature is that strap, complete with the chamber that may be filled, be in the form of a strip, which will allow the minimally invasive emplacement of the strap, without opening of the abdominal cavity being required.

Figure 14:
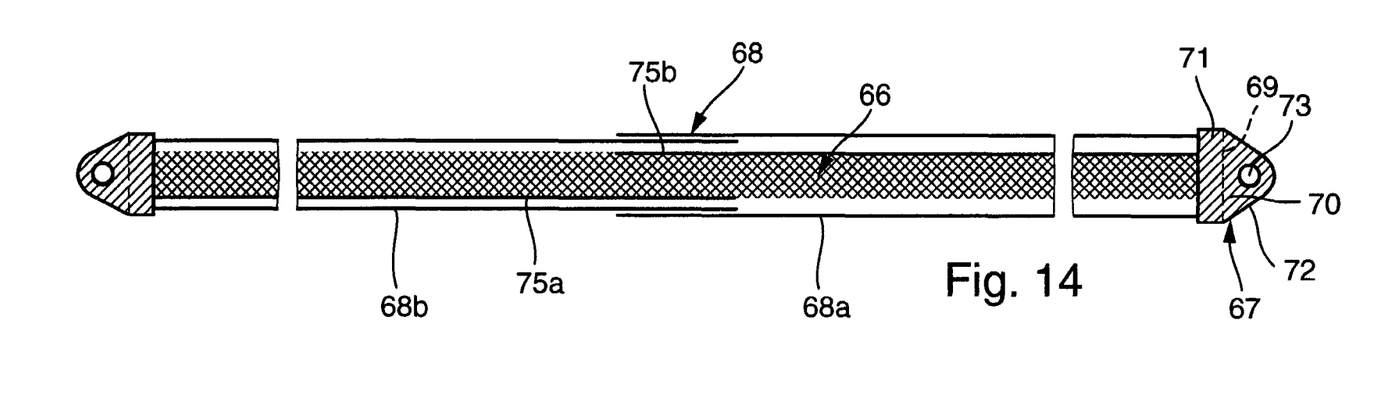
FIG. 14: an embodiment of an incontinence strap according to the invention having reinforced attachment devices.

FIG. 14 depicts another embodiment of an incontinence strap 66 according to the invention. This incontinence strap is preferably configured such that it is elastic and porous, in particular, configured such that it consists of knit fabric, which will allow the ingrowth of tissue. This incontinence strap 66 has an attachment device 67 on each end. These attachment devices are in the form of blunted tips. This will allow them to be easily guided through tissue in the desired directions, more safely than would be the case if they had corners or edges. Both attachment devices are identically configured. The incontinence strap 66 also has an enshrouding sheath 68 that is configured such that it may be withdrawn therefrom due to the fact that it consists of two, separate segments (68a, 68b), one of which is preferably inserted into the other at the middle of the strap, and overlaps the other. However, the sheath may also be a one-piece construction, in which case it will have a perforation, preferably at its middle, that will simplify its separation into two segments. This sheath preferably consists of a thermoplastic material, in particular, polyethylene. These sheaths simplify inserting the strap and protect it against contamination.

The attachment devices 67 are of multilayered construction. The upper layer consists of a casing 69 that surrounds the sheath 68 in the vicinities of its attachment devices. Lying below, i.e., inward from, this casing 69 is a second layer, i.e., the sheath 68. Another layer 70 of thermally bondable material lies beneath the sheath 68, i.e., between the sheath 68 and the strap 66. A final layer, i.e., the incontinence strap 66 itself, lies below this layer 70. The strap 66, the layer 70, the sheath 68, and the casing 69 are bonded together at the extremities of the incontinence strap. A rear section 71 of the attachment devices 67 is left unbonded. The strap is bonded and reinforced over its full width, which will prevent its knit fabric from tearing off the laminate. A through hole 73 that may be punched during bonding in order that its edges will be compression bonded when the through hole is punched is situated within the bonded section 72 of the laminate. The punched through hole may have various shapes, such as a triangular, rectangular, square, or, preferably, a circular or an elongated oval, shape.

Each segment 68a and 68b of the sheath also has an asymmetrically arranged, identifying line 75a and 75b. These identifying lines preferably have a readily recognized coloration. Within the overlapping sections of the pair of transparent segments 68a and 68b of the sheath, which preferably lie in the vicinity of the middle of the strap, the two identifying lines 75a and 75b are parallel to one another in order that the operator may recognize the middle of the strap.

All materials employed are preferably thermoplastic materials. The strap itself preferably consists of polypropylene, and, as mentioned above, the sheath preferably consists of, for example, polyethylene. The film thickness of the casing 69 and the layer 70 of bondable materials preferably exceeds the film thickness of the sheath 68. It will be beneficial if the sheath 68 has a film thickness of about 70 µm. The film thicknesses of the casing 69 and layer 70 of bondable material should preferably be about 200 µm.

Figure 15:
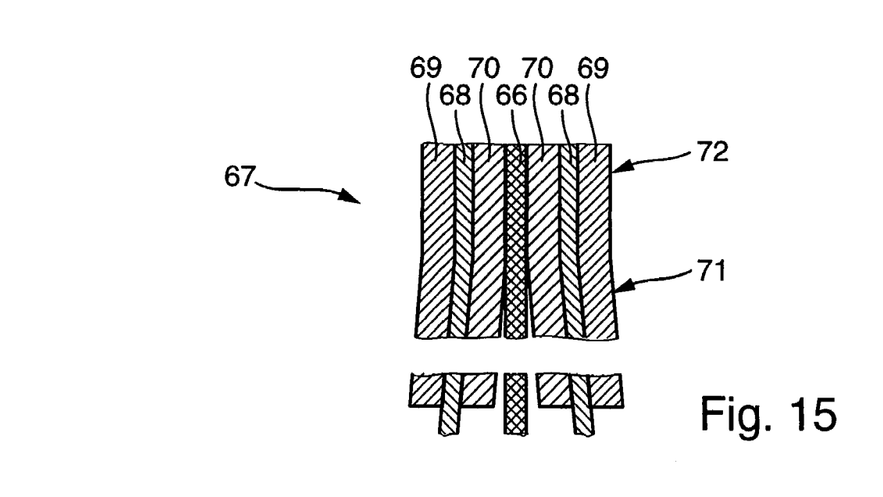
FIG. 15: a longitudinal section through the strap shown in FIG. 14, where the sectioning is along the line A-A' indicated in FIG. 14, drawn on a much larger scale.

FIG. 15 depicts a longitudinal section through the attachment device 67 at the transition zone between its bonded section 72 and unbonded section 71, drawn on a much larger scale. The incontinence strap 66 is situated at the center of the attachment device 67. The incontinence strap 66 is sandwiched between two layers 70 of bondable material. These layers of bondable material are followed by the sheath 68. The film thickness of the sheath 68 is much less than that of the layers 70 of bondable material. The outer faces of the attachment device 67 are bounded by the casing 69. The film thickness of the casing 69 is approximately equal to the film thickness of the layers of bondable material. Within section 72, the aforementioned layers are thermally bonded together by welding covering an extended area. Within section 71, these layers are not unbonded together. However, it would be feasible to also bond, e.g., pointwise bond, these layers together, within section 71. Following implantation, the attachment devices, together with the ends of the strap, may be cut off and the segments 68*a* and 68*b* of the sheath withdrawn along opposing directions. It will also be feasible to cut off just one half of the sheath and the ends of the strap, together with the attachment devices, and withdraw the ends of the strap, together with the segments of the sheath, along opposing directions.

Figure 16A:
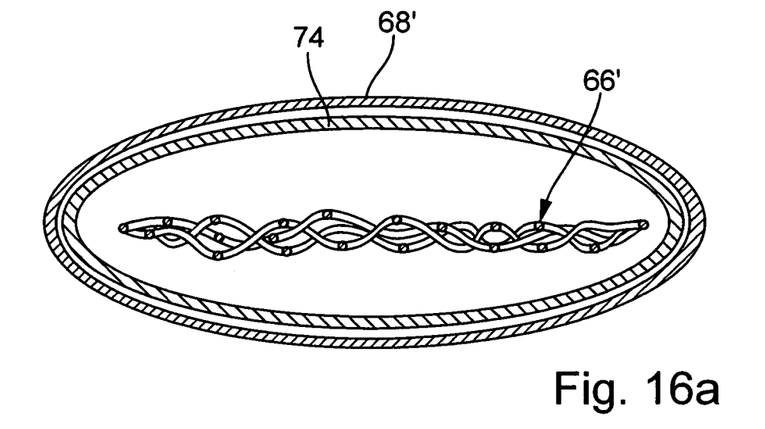
FIG. 16a: a schematized view of the cross-section of an unbonded section of another embodiment of an incontinence strap according to the invention.

FIG. 16*a* depicts a schematized view of the cross-section of an, as yet, unbonded section of the ends of another embodiment of an incontinence strap according to the invention. The incontinence strap 66' and sheath 68' have an overall length of 31 cm and a width of 2 cm. As has already been mentioned in conjunction with the descriptions of FIGS. 14 and 15, the incontinence strap 66' is knitted and has pores, which will allow ingrowth of tissue. The ends of the incontinence strap 66' is encased in a casing 74 that has a length falling within the range 2 cm to 8 cm. The casing 74 is, in turn, encased in the sheath 68', which has already been described in conjunction with the preceding example of an embodiment. The casing 74, which is arranged between the sheath 68' and the end of the strap, encloses only a few centimeters of the long ends of the incontinence strap and serves as reinforcing material. The casing 74 has a lower melting point than the incontinence strap 66'. That property of the casing 74 will allow it to act as a thermoplastic bond joining the sheath to the incontinence strap 66' in the vicinities of the attachment devices (cf. FIG. 16*b*) and effect a certain strengthening of the strap within the adjacent unbonded sections. The sheath 68' has a film thickness of about 70 µm and the casing 74 has a film thickness of about 200 µm. Both the sheath 68' and the casing 74 consist of polyethylene.

Figure 16B:
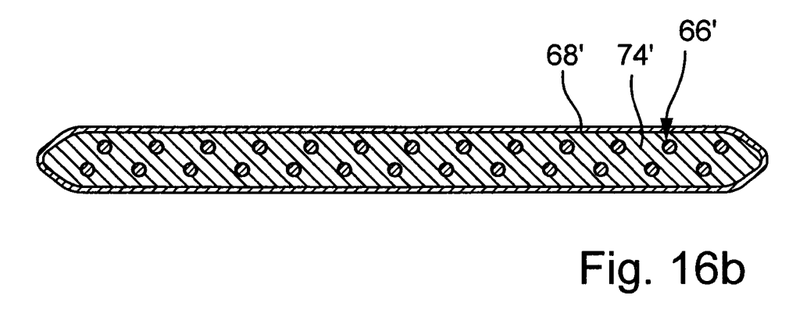
FIG. 16b: a schematized view of the cross-section of the incontinence strap shown in FIG. 16a in the vicinity of an attachment device, i.e., of a bonded section thereof.

FIG. 16*b* depicts a schematized view of the cross-section of the incontinence strap shown in FIG. 16*a* in the vicinity of an attachment device, i.e., of a bonded section thereof. Pressure and thermal treatment of the incontinence strap 66', including its encasings, in the vicinities of its long ends have provided that its casing has melted and acts as a thermoplastic bond 74' joining the sheath 68' to the incontinence strap 66'. In addition to acting as an adhesive, the material 74' of the casing also acts as a filler for filling the pores of the incontinence strap 66'. In the case of this example of an embodiment as well, a through hole is situated within the bonded section, which, however, has not been depicted here.

The total thickness of the laminate in the vicinity of the attachment device is about 650 µm.

The invention claimed is:

1. An incontinence strap for treating urinary incontinence having two ends,
    wherein the incontinence strap is configured such that the incontinence strap is porous and flexible and arranged in a sheath,
    wherein each of the two ends of the strap have at least one attachment device,
    wherein the incontinence strap is reinforced in the vicinity of the at least one attachment device with a reinforcement, the reinforcement being formed by thermal bonding to the sheath thereby forming a ply,
    wherein another material is thermally bonded to the incontinence strap forming another ply,
    wherein the ends of the incontinence strap are encased in a casing which serves as a reinforcing material which in turn is encased in the sheath,
    wherein the casing has a lower melting point than the incontinence strap and acts as a thermoplastic bond joining the sheath to the incontinence strap in the vicinity of the attachment devices and acts as a filler for filling pores of the incontinence strap, and
    wherein the attachment devices have punched through holes.

2. An incontinence strap according to claim 1, wherein the incontinence strap is configured such that at least one member of the group consisting of materials employed and construction differs over the length of the incontinence strap.

3. An incontinence strap according to claim 1, wherein a longitudinal midsection of the incontinence strap, that is intended for arrangement in the vicinity of the urethra, differs from the remainder of the strap in at least one member of the group consisting of structure and material.

4. An incontinence strap according to claim 1, wherein the incontinence strap at least partially consists of resorbable material.

5. An incontinence strap according to claim 3, wherein the longitudinal midsection of the incontinence strap at least partially consists of resorbable material.

6. An incontinence strap according to claim 4, wherein the resorbable material at least partially consists of polyvinyl alcohol.

7. An incontinence strap according to claim 3, wherein at least the longitudinal midsection of the incontinence strap has smooth lateral edges.

8. An incontinence strap according to claim 3, wherein at least the longitudinal midsection of the incontinence strap has a smooth outer surface.

9. An incontinence strap according to claim 3, wherein the longitudinal midsection of the incontinence strap is at least one of the group consisting of wider and thicker than the remainder of the strap.

10. An incontinence strap according to claim 3, wherein the incontinence strap is configured such that its thickness may be varied, at least over its longitudinal midsection.

11. An incontinence strap according to claim 3, wherein the incontinence strap is configured such that at least its longitudinal midsection is double-walled.

12. An incontinence strap according to claim 3, wherein the incontinence strap is configured such that at least its longitudinal midsection is tubular.

13. An incontinence strap according to claim 3, wherein the incontinence strap is configured such that at least its longitudinal midsection is in the form of a chamber that may be filled with a fluid.

14. An incontinence strap according to claim 13, wherein the chamber that may be filled with fluid has a fluid line extending to at least one end of the strap.

15. An incontinence strap according to claim 13, wherein the walls of the chamber that may be filled with fluid at least partially consists of pierceable, self-sealing material.

16. An incontinence strap according to claim 14, wherein the fluid line at least partially consists of pierceable, self-sealing material.

17. An incontinence strap according to claim 1, wherein the incontinence strap has at least one of the group consisting of an outer surface and construction that promotes a self-anchoring in the abdominal wall in the vicinities of the ends of the incontinence strap.

18. An incontinence strap according to claim 1, wherein both of the ends of the incontinence strap are configured for attaching the incontinence strap to a curved shaft, for emplacing the incontinence strap in the abdominal cavity.

19. An incontinence strap according to claim 1, wherein the incontinence strap is narrower at the ends of the strap than in the other regions.

20. An incontinence strap according to claim 18, wherein the incontinence strap is attachable to the shaft such that the incontinence strap cannot twist.

21. An incontinence strap according to claim 18, wherein the incontinence strap is attachable to the shaft such that the incontinence strap lies in a plane aligned on the shaft.

22. An incontinence strap according to claim 18, wherein the incontinence strap is attachable to the shaft such that the incontinence strap will have a cross-section predetermined by the flat shape of the incontinence strap.

23. An incontinence strap according to claim 18, wherein the incontinence strap is attached to a coupler that is attachable to the shaft.

24. An incontinence strap according to claim 18, wherein the incontinence strap is attachable to the shaft such that the incontinence strap cannot subsequently be detached therefrom.

25. An incontinence strap according to claim 1, wherein the sheath is arranged to have a midsection that is transversely split, or is transversely splittable, and is withdrawable over the ends of the strap following implantation of the strap.

26. An incontinence strap according to claim 18, wherein at least one shaft is allocated to the incontinence strap for the purpose of inserting the strap into the patient's lower abdomen.

27. An incontinence strap according to claim 1, wherein at least the sheath is folded over and thermally bonded to the incontinence strap in order to reinforce the incontinence strap in the vicinity of the at least one attachment device.

28. An incontinence strap according to claim 1, wherein the strap is encased by at least one casing and is at least partially thermally bonded thereto in the vicinity of the at least one attachment device.

29. An incontinence strap according to claim 1, wherein an at least one additional ply of thermally bondable material(s) is/are employed for reinforcing the incontinence strap in the vicinity of the at least one attachment device.

30. An incontinence strap according to claim 25, wherein an at least one additional ply of thermally bondable material(s) is/are employed and has a film thickness exceeding that of the sheath.

31. An incontinence strap according to claim 1, wherein the thermal bonding covers an extended area.

32. An incontinence strap according to claim 1, wherein the thermal bonding is formed from point bonds.

33. An incontinence strap according to claim 1, wherein the thermal bonding is formed from partial bonds, each of which covers an extended area.

34. An incontinence strap according to claim 1, wherein the thermal bonding is a combination of bonding covering an extended area, a partial area and points whereby the at least one attachment device thus has spatially varying flexibilities.

35. An incontinence strap according to claim 1, wherein the thermal bonding is a combination of bonding covering an extended area, a partial area and points whereby the attachment device is stiffer at the center of the at least one attachment device than at the edges of the attachment device and thus has spatially varying flexibilities.

36. An incontinence strap according to claim 25, wherein the width of the incontinence strap in the vicinity of the at least one attachment device is at a maximum equal to the width of the sheath outside the reinforced section of the incontinence strap.

37. An incontinence strap according to claim 25, wherein at least the sheath and any other material or other plies that may be employed consist of thermoplastic material.

38. An incontinence strap according to claim 1, wherein the incontinence strap consists of thermoplastic material whose melting range lies at temperatures exceeding those of the melting range of a ply lying on the strap.

39. An incontinence strap according to claim 1, wherein the incontinence strap consists of various polymeric materials that are in the form of a textured foil or a fabric.

40. An incontinence strap according to claim 25 wherein the sheath, that is transversely split at the midsection of the sheath, is transparent and has mutually overlapping ends, and each segment thereof exhibits asymmetrically arranged, identifying, longitudinal lines that become double lines in the vicinity of the overlapping ends of the sheath.

41. An incontinence strap according to claim 29, wherein the at least one additional ply has a film thickness exceeding that of the sheath.

42. An incontinence strap according to claim 29, wherein at least the sheath and any other material or other plies that may be employed consist of thermoplastic material.

* * * * *